United States Patent [19]

Marker

[11] Patent Number: 5,399,788
[45] Date of Patent: Mar. 21, 1995

[54] TWO-STAGE PROCESS FOR PRODUCING DIISOPROPYL ETHER USING HYDRATION

[75] Inventor: Terry L. Marker, Warrenville, Ill.

[73] Assignee: UOP, Des Plaines, Ill.

[21] Appl. No.: 171,573

[22] Filed: Dec. 22, 1993

[51] Int. Cl.$^6$ .............................................. C07C 41/06
[52] U.S. Cl. .................... 568/697; 568/907
[58] Field of Search ............................. 568/697, 907

[56] References Cited

U.S. PATENT DOCUMENTS

| | | | |
|---|---|---|---|
| 4,214,107 | 7/1980 | Chang et al. | 568/897 |
| 4,499,313 | 2/1985 | Okumura et al. | 568/897 |
| 4,857,664 | 8/1989 | Huang et al. | 568/695 |
| 4,906,787 | 3/1960 | Huang et al. | 568/697 |

Primary Examiner—Howard T. Mars
Attorney, Agent, or Firm—Thomas K. McBride; John F. Spears, Jr.; Reginald K. Taylor

[57] ABSTRACT

In process for the production of diisopropyl ether, a propylene-containing stream is contacted with isopropyl alcohol in a first stage in the presence of a catalyst under conditions to produce an effluent stream comprising diisopropyl ether. At least a portion of this effluent stream is recycled to a second stage where the diisopropyl ether is reacted with water to produce isopropyl alcohol. The isopropyl alcohol is then recycled to the first stage. The benefit of producing isopropyl alcohol by the hydration of diisopropyl ether is that it is an easier reaction than, for example, the hydration of propylene. As a result, the process of the present invention can operate under less severe conditions, i.e., less cost.

11 Claims, 1 Drawing Sheet

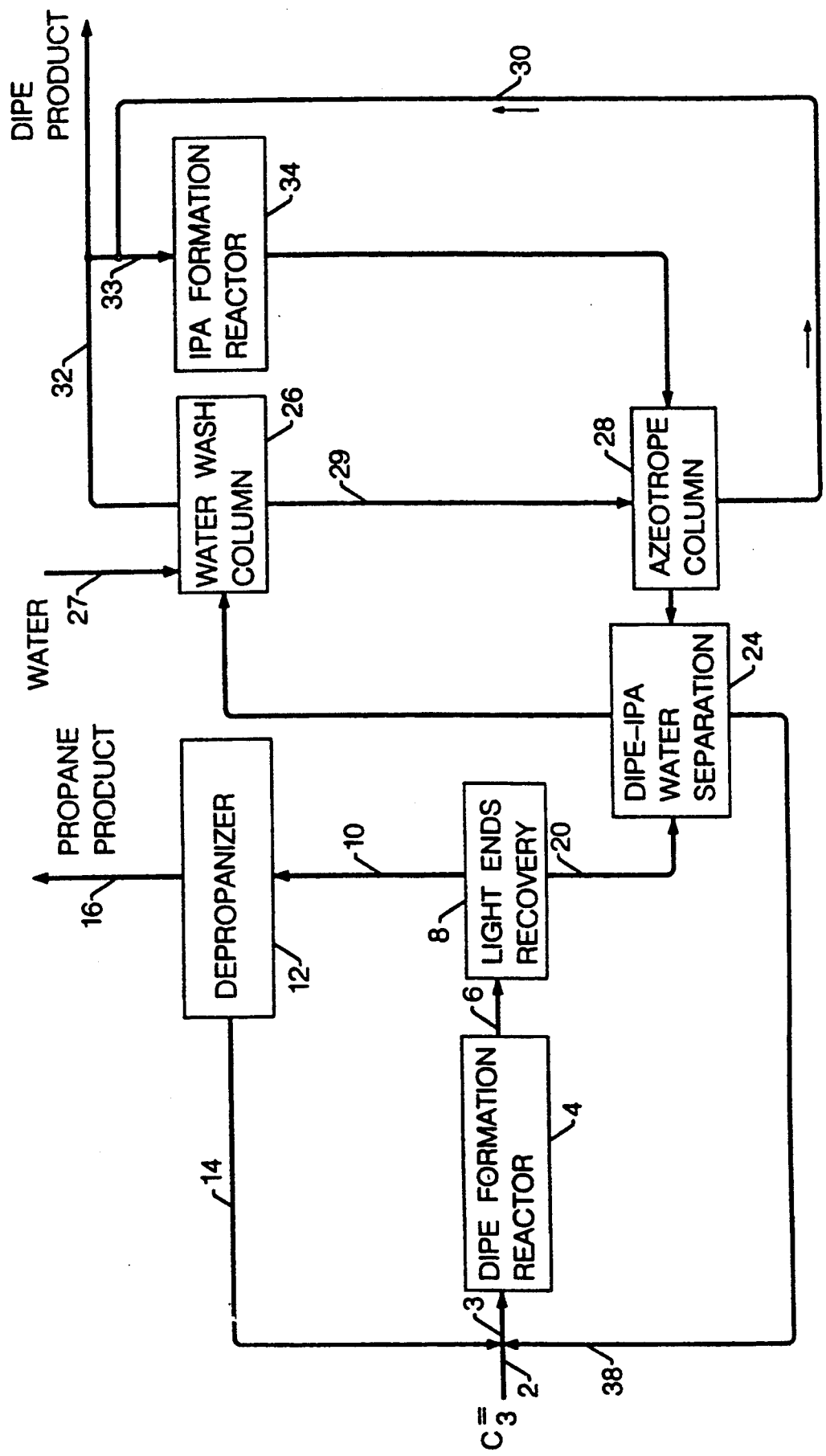

TWO-STAGE PROCESS FOR PRODUCING DIISOPROPYL ETHER USING HYDRATION

FIELD OF THE INVENTION

The present invention relates to a two-stage process for producing diisopropyl ether (DIPE). In the first stage, isopropyl alcohol (IPA) is reacted with propylene to form DIPE. In the second stage, at least a portion of the DIPE that was formed in the first stage is hydrated to form IPA. At least a portion of the IPA formed in the second stage is recycled to the first stage to form DIPE.

BACKGROUND OF THE INVENTION

The need to eliminate lead-based octane enhancers in gasoline has provided an incentive for the development of processes to produce high octane gasolines blended with lower aliphatic octane boosters. Supplementary fuels are being examined by the petroleum refining industry. Lower molecular weight alcohols and ethers, such as isopropyl alcohol (IPA) and diisopropyl ether (DIPE), are in the boiling range of gasoline fuels and are known to have a high blending octane number. They are also useful as octane enhancers. In addition, by-product propylene from which IPA and DIPE can be made is usually available in a fuels refinery, typically as a $C_3$ aliphatic stream which is rich in both propylene and propane.

In the past, IPA and DIPE were produced using the so-called indirect hydration processes. In the indirect hydration process, a selected olefin feed is absorbed in a concentrated sulfuric acid stream to form an extract containing the corresponding alkyl ester of the sulfuric acid. Thereafter, water is admixed with the ester-containing extract to hydrolyze the ester and to form the desired alcohol and ether which are then recovered, generally by stripping with steam or some other heating fluid. A diluted sulfuric acid stream is thereby produced. This acid stream is then generally treated to concentrate the sulfuric acid stream for recycle to the absorption stage.

In the indirect hydration process, the use of sulfuric acid as a catalyst presents certain problems. First, severe corrosion of process equipment can occur. Second, separating the produced ether from the sulfuric acid can be difficult. Third, a substantial quantity of waste sulfuric acid is produced in the concentration of the catalyst for recovery. Because of these problems, it has been found that the process of synthesizing DIPE by using concentrated sulfuric acid is not commercially viable. Clearly, there was a need for a more direct manner of bringing about the hydration reaction.

This need was addressed by so-called direct hydration processes using solid catalysts. In the direct hydration process, an olefinic hydrocarbon such as propylene is reacted directly with water over a solid hydration catalyst to produce an intermediate IPA stream from which the product DIPE can be formed. Development work using direct hydration focuses on the use of solid catalysts such as active charcoal, clays, resins and zeolites. Examples of olefin hydration processes which employ zeolite catalysts as the hydration catalyst can be found in U.S. Pat. Nos. 4,214,107, 4,499,313, 4,857,664 and 4,906,787.

The use of zeolites as hydration catalysts has the disadvantage of being expensive in comparison to other catalysts, for example, ion exchange resin catalysts. Also, in comparison to ion exchange resin catalysts zeolites do not operate as well at the relatively low temperatures required for hydration and etherification. Furthermore, zeolites have a strong tendency to form DIPE from reaction (2) instead of reaction (1). They also have a strong tendency to produce substantial amounts of undesirable polygasoline from the reaction of propylene with itself.

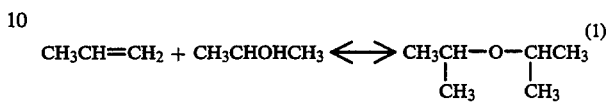

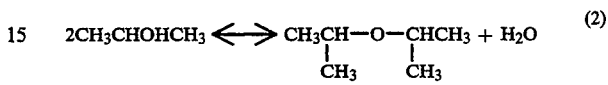

The preparation of DIPE from propylene can proceed by multiple chemical reaction sequences. Depending on the sequence used, the cost associated therewith can be a problem. In one sequence, propylene is hydrated to form IPA which is reacted with additional propylene to form diisopropyl ether. The hydration of propylene to form IPA is a difficult reaction to perform because, in their normal states, propylene is a gas and water is a liquid. Accordingly, the reaction of the two phases requires severe conditions, for example, a pressure of 1000 psig. Further, since the solubility of propylene in water is poor, severe conditions such as a pressure of 1000 psig–1500 psig are required to make this reaction work effectively. As a result, the hydration of propylene to form IPA is expensive.

SUMMARY OF THE INVENTION

The present invention solves the above-identified problems by establishing a two-stage operation. In the first stage, diisopropyl ether is produced by reacting a part of the propylene with isopropyl alcohol. In the second stage, isopropyl alcohol is produced by reacting diisopropyl ether recovered from the first stage with water, i.e., hydration of diisopropyl ether. In this way, the above-described problems associated with forming isopropyl alcohol through hydration of propylene are avoided. A benefit of the present invention is that the formation of isopropyl alcohol by hydration of diisopropyl ether is not as difficult as the formation of isopropyl alcohol by hydration of propylene. One reason for this is that in their normal states, both diisopropyl ether and water are liquids. This is important because it allows for more intimate contact in the reaction zone. Another reason is that the solubility of diisopropyl ether in water is better than the solubility of propylene in water. As a result, the present invention can be carried out under less severe operating conditions, e.g., lower pressure. Another benefit of the present invention is the propylene purity required for the etherification of isopropyl alcohol is less than that required for the hydration of propylene. This is because IPA is soluble in $C_3=$ and they are in liquid phase. Accordingly, the need for a large fractionation column to produce high purity propylene is avoided.

The present invention is a two-stage process for the production of diisopropyl ether which process comprises the steps of: in a first stage, reacting a propylene-containing stream with an isopropyl alcohol recycle stream in the presence of a catalyst in a diisopropyl ether formation reactor under conditions to produce a first stage effluent stream comprising diisopropyl ether and unreacted propylene and isopropyl alcohol; passing at least a portion of the first stage effluent stream to a diisopropyl ether/isopropyl alcohol/water separation zone to produce a diisopropyl ether product stream and the isopropyl alcohol recycle stream; in a second stage, reacting at least a portion of the diisopropyl ether product stream with water in the presence of a catalyst in an isopropyl alcohol formation reactor under conditions sufficient to produce a second stage effluent stream comprising isopropyl alcohol and water; passing at least a portion of the second stage effluent stream to the diisopropyl ether/isopropyl alcohol/water separation zone; and recycling at least a portion of the isopropyl alcohol recycle stream to the first stage.

In one embodiment, the present invention is a two-stage process for the production of diisopropyl ether which process comprises the steps of: in a first stage, reacting a propylene-containing stream having a propylene concentration of not more than about 75 wt. % with an isopropyl alcohol recycle stream in the presence of a catalyst in a diisopropyl ether formation reactor under conditions to produce a first stage effluent stream comprising diisopropyl ether and unreacted propylene and isopropyl alcohol; passing at least a portion of the first stage effluent stream to a diisopropyl ether/isopropyl alcohol/water separation zone to produce a diisopropyl ether product stream and the isopropyl alcohol recycle stream having a water concentration of less than about 3 wt. %; in a second stage, reacting at least a portion of the diisopropyl ether product stream with water in the presence of a catalyst in an isopropyl alcohol formation reactor under conditions sufficient to produce a second stage effluent stream comprising isopropyl alcohol and water; passing at least a portion of the second stage effluent stream to the diisopropyl ether/isopropyl alcohol/water separation zone; and recycling at least a portion of the isopropyl alcohol recycle stream to the first stage.

In another embodiment, the present invention is a two-stage process for the production of diisopropyl ether which process comprises the steps of: in a first stage, reacting a propylene-containing stream having a propylene concentration of not more than about 75 wt. % with an isopropyl alcohol recycle stream in the presence of a catalyst in a diisopropyl ether formation reactor under conditions to produce a first stage effluent stream comprising diisopropyl ether and unreacted propylene and isopropyl alcohol; passing at least a portion of the first stage effluent stream to a light ends recovery zone to produce a propylene/propane overhead mixture and a light ends recovery zone effluent stream; passing the propylene/propane overhead mixture to a depropanizer zone to produce a propylene recycle stream; passing the propylene recycle stream to the first stage; passing at least a portion of the light ends recovery effluent stream to a diisopropyl ether/isopropyl alcohol/water removal zone to produce a diisopropyl ether/isopropyl alcohol/water removal zone effluent stream and the isopropyl alcohol recycle stream having a water concentration of less than about 3 wt. %; passing at least a portion of the diisopropyl ether/isopropyl alcohol/water removal zone effluent stream to a water wash zone to produce a diisopropyl ether product stream and a water wash effluent stream comprising isopropyl alcohol and water; passing at least a portion of the water wash effluent stream to an azeotrope column to produce an azeotrope column effluent stream comprising water; in a second stage, passing the azeotrope effluent stream to an isopropyl alcohol formation reactor and reacting at least a portion of the diisopropyl ether product stream in the presence of a catalyst in the isopropyl alcohol formation reactor under conditions sufficient to produce a second stage effluent stream comprising isopropyl alcohol and water; passing at least a portion of the second stage effluent stream to the diisopropyl ether/isopropyl alcohol/water separation zone; and recycling at least a portion of the isopropyl alcohol recycle stream to the first stage.

DESCRIPTION OF THE DRAWING

The FIGURE is a schematic representation of one embodiment of the present invention.

DESCRIPTION OF THE PREFERRED EMBODIMENT

The present invention is a two stage process for producing DIPE. In the first stage, a propylene-containing stream is reacted with an IPA recycle stream in the presence of a catalyst in a diisopropyl ether formation reactor under conditions sufficient to produce a first stage effluent stream comprising DIPE and unreacted propylene and IPA.

Suitable sources for the propylene-containing stream include, but are not limited to, gas plant off-gas containing propylene, naphtha cracker off-gas containing light olefins, and refinery fluidized catalytic cracked (FCC) propane/propylene streams. The concentration of propylene used will vary depending upon the source of the propylene. These sources provide a propylene/propane mixture comprising about 60–80 vol. % propylene. In one embodiment of the present invention, the propylene concentration of the propylene-containing stream is not more than about 75 wt. %.

The catalyst used in the first stage of the present invention can be any catalyst suitable for olefin conversion. Suitable catalysts include zeolites and ion exchange resins. With respect to zeolites, both intermediate and large pore zeolites can be used. Of particular interest for use herein are large pore acidic zeolites, e.g. zeolite Beta, X, L, Y, ultra stable Y, rare earth Y, ZSM-3, ZSM-4, ZSM-12, ZSM-20, and ZSM-50.

With respect to the ion exchange resin, a synthetic ion exchange resin is preferred. The preferred ion exchange resin has three components: (1) the raw material which is used for the construction of the skeleton or matrix; (2) bridging agents for crosslinking and insolubilization; and (3) the type and number of functional or iongenic active groups.

With respect to forming the ion exchange resin matrix, polymerization and polycondensation can be used as the synthesis route. Polymerization is preferred because the matrices resulting therefrom generally have higher chemical and thermal stability. The preferred starting material for synthesizing the catalyst of the present invention is styrene. The styrene is polymerized with itself and with divinylbenzene into a polymeric molecule:

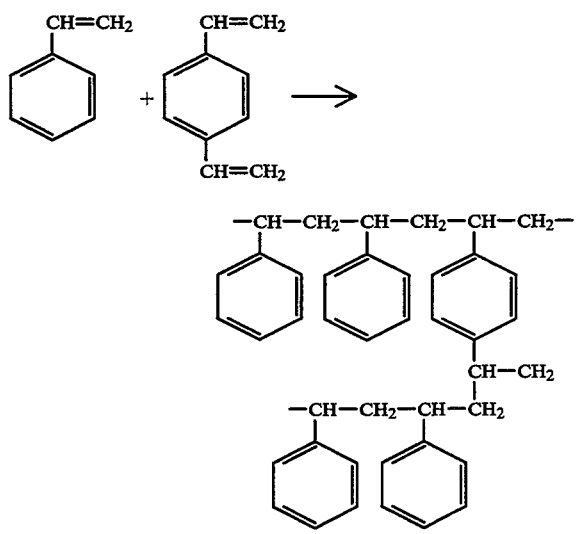

Matrices for the catalyst of the present invention can also be prepared using: (1) in divinylbenzene and acrylic acid or methacrylic acid or;

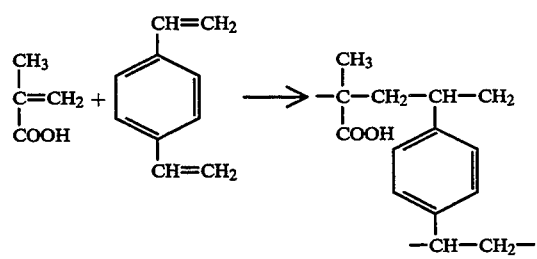

(2) phenol and formaldehyde;

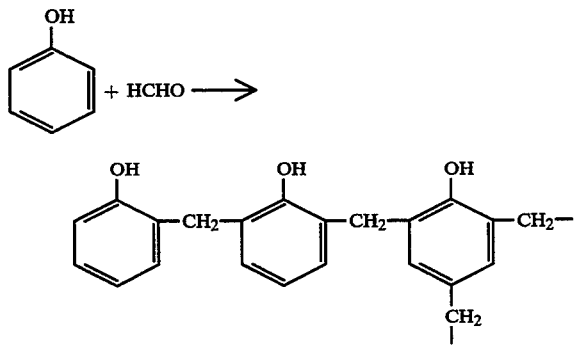

In the case of divinylbenzene-containing matrices, crosslinking depends on the quantity of divinylbenzene used as the crosslinking agent. The nature and degree of crosslinking can have a profound effect on the ion exchange properties of the catalyst. The amount of divinylbenzene used can range from about 2 to 12 wt. %. With respect to the structure of the network of synthetic resin ion exchangers, different types are now available with designations such as gel, macroporous, and isoporous ion exchange. With respect to gel-type ion exchangers, during polymerization of styrene and divinylbenzene, the network formed is obtained as a gel. The properties of such co-polymer can be varied by changing the ratios of the amounts of the individual monomers used during the synthesis. These gel-type polymer structures have no appreciable porosity until they are swollen in suitable medium; but such crosslinked polymers swell to a well-defined and reproducible degree in an appropriate solvent system, such as toluene. Macroporous ion exchangers are types in which a solvent is used during production from the monomers so that a porous matrix structure is formed in the course of polymerization. The isoporous ion exchangers are a group in which the crosslinking and pore size are modified in a way to obtain polymers with a substantially uniform pore size.

In a preferred embodiment, the first stage catalyst is a cation exchanger resin comprising $SO_3H$ groups. Suitable cation exchangers include, for example, sulfonated organic resins in their acidic form. Of particular importance are sulfonated polystyrene resins, such as the $SO_3H$ groups containing co-polymers of aromatic monovinyl compounds and aromatic polyvinyl compounds. Especially preferred cation exchangers are sulfonated styrene/divinylbenzene co-polymers, for example, "Amberlyst 36." These cation exchangers are produced by the sulfonation of suspension co-polymer beads with sulfuric acid, sulfur trioxide, fuming sulfuric acid or chlorosulfonic acid. The $SO_3$ groups which are the ionic groups yielding the cation exchange function can be in the para position.

The first stage catalyst can have a surface area of about 1–100 $m^2/g$, preferably approximately 35 and a porosity of about 0.05 to 0.5 ml/g, preferably 0.30 ml/g.

Suitable conditions for the first stage include a temperature of about 200°–300° F., a pressure of about 100–1200 psi, preferably about 700–1000 psi, and an IPA to propylene ratio of about 0.1:1 to 2:1, preferably about 0.6.

In the first stage, etherification can be carried out under dense phase, liquid phase, vapor phase or mixed vapor-liquid phase conditions in batch or continuous manner. With respect to the first stage DIPE formation reactor, a stirred tank reactor or fixed bed reactor can be employed. The flow of reactants and products can be liquid-upflow, liquid-downflow, countercurrent, or cocurrent, a liquid hourly space velocity of about 0.1 to 20, preferably about 0.1 to 2 when operating in the continuous mode. In a preferred embodiment, the first stage DIPE formation reactor can be a liquid phase fixed-bed reactor with recirculation of cooled etherification zone effluent for temperature control.

Exiting the first stage DIPE formation reactor is an effluent comprising DIPE, unreacted propylene, propane, and unreacted IPA. In one embodiment of the present invention, the first stage effluent stream is passed to a light ends recovery zone where propylene and propane can be separated from the DIPE and unreacted IPA. The light ends recovery zone can consist of at least one fractionation tower operated at temperatures in the range of about 110°–350° F. and pressures in the range of about 225 psig. In one embodiment of the present invention, a light ends recovery zone overhead stream comprising a substantial amount of the propylene and propane is passed to a depropanizer. In the depropanizer, propylene is separated from propane by fractionation. This separation is important because it allows for: (1) the production of a propane product stream and; (2) the recycle of unreacted propylene to the first stage DIPE formation reactor.

The effluent from the light ends recovery zone which comprises both DIPE and IPA can be passed to a DIPE-IPA water removal zone. In this DIPE-IPA water removal zone, a DIPE product stream, an isopropyl alcohol recycle stream and a water stream are produced. Operating conditions for the DIPE-IPA water removal zone include a temperature of about 120°–222° F. and pressure of about 35 psig. In a preferred embodiment, a DIPE-IPA water removal zone effluent stream comprising DIPE and low levels of IPA proceeds to a water wash zone which removes the last traces of IPA. The effluent from the water wash zone which contains IPA and water is sent to an azeotrope column which produces an azeotrope column effluent stream which is sent to the second stage IPA formation reactor (which will be described in more detail below) and an azeotropic mixture of water and IPA which is sent back to the DIPE-IPA water removal zone so that the IPA can be separated from the water and recycled to the first stage DIPE formation reactor.

Regardless of whether the first stage effluent stream is treated to remove light ends or residual IPA, an essential feature of the present invention is passing at least a portion of the DIPE contained in the first stage effluent stream to a second stage IPA formation reactor where DIPE is reacted with water in the presence of a catalyst under conditions sufficient to produce a second stage effluent stream comprising IP, water and a small amount of DIPE.

The catalyst suitable for use in the second stage of the process of the present invention is the same catalyst type described hereinabove with respect to the first stage catalyst, although a catalyst which is more suitable for reaction with high levels of water and at hotter temperatures is more preferred.

Suitable conditions for the second stage include a temperature of about 250°–350° F., a pressure of about 100–500 psig, preferably about 300–400 psig, and a water to DIPE ratio of about 1:1 to 50:1, preferably about 10:1.

In the second stage IPA formation reactor, hydration can be carried out under dense phase, liquid phase, vapor phase or mixed vapor-liquid phase conditions in batch or continuous manner. Further, with respect to the second stage IPA formation reactor, a stirred tank reactor or fixed bed reactor can be employed. The flow of reactants and products can be trickle-bed, liquid-upflow, liquid-downflow, countercurrent, or cocurrent having a liquid hourly space velocity of about 0.05 to 20, preferably about 0.1 to 2 when operating in the continuous mode. In a preferred embodiment, the second stage IPA formation reactor can be a liquid phase, fixed-bed, upflow reactor with recirculation of the DIPE phase.

At least a portion of the effluent from the second stage IPA formation reactor is passed to the DIPE-IPA water removal zone where the IPA can be separated from the water and recycled to the first stage DIPE formation reactor.

Referring to the drawing, propylene in stream 2 is contacted with recycled IPA in stream 38 and the combined feed is fed to a first stage DIPE formation reactor 4 through line 3. In DIPE formation reactor 4, recycled IPA is reacted with propylene to form DIPE at a temperature of about 250° F. and a pressure of about 800 psig.

Exiting DIPE formation reactor 4 is a first stage effluent stream 6 which comprises DIPE and unreacted propylene and IPA is routed to light ends recovery zone 8. In light ends recovery zone 8, propane and propylene are removed from the first stage effluent stream 6 at a temperature of about 113°–350° F. and a pressure of about 240 psig.

A propylene/propane overhead mixture exits the top of light ends recovery zone 8 in stream 10 and enters depropanizer 12. Depropanizer 12 is operated at a temperature of about 135° F. and a pressure of about 295–305 psig. A propylene recycle stream 14 rich in propylene (55–70%) and containing a small amount of propane is removed from the top of depropanizer 12 and passed to DIPE formation reactor 4. A propane product stream 16 exits depropanizer 12 at the bottom.

Effluent from light ends recovery zone 8 is sent to a DIPE-IPA water removal zone 22 via line 20. This DIPE-IPA water separation zone 22 comprises DIPE-IPA water removal column 24, water wash column 26, and azeotrope column 28. DIPE-IPA water removal column 24 serves both as a vessel for separating DIPE and IPA and as a drying column for removing water. Accordingly, exiting the bottom of DIPE-IPA water removal column 24 in stream 38 is an IPA recycle stream that is essentially free of water (contains less than 3%). This stream (38) is recycled to first stage DIPE formation reactor 4. Exiting the top of DIPE-IPA water removal column 24 is a DIPE-IPA water removal effluent stream 25 comprising a DIPE phase and a small amount of IPA. Also exiting is a separate water phase which separates out as a separate phase in the overhead receiver. This is recycled back to the azeotrope column.

In order to render this DIPE phase free of IPA, stream 25 is passed to water wash column 26 where IPA is transferred from the DIPE phase to a water phase. Water enters water wash column 26 in line 27 and a water wash effluent stream comprising water and IPA exits water wash column 26 in line 29. This aqueous stream 29 is passed to azeotrope column 28. Two streams exit azeotrope column 28. At the bottom of column 28, an azeotrope column effluent stream containing a substantial amount of the water used in the water wash column 26 is removed. A side stream 31 containing a mixture of IPA and water is passed to DIPE-IPA water removal column 24 so that the IPA can be separated and recycled to the first stage DIPE formation reactor.

A DIPE product stream 32 exits water wash column 26 substantially free of IPA. At least a portion of the DIPE product stream 32 is admixed with at least a portion of azeotrope column effluent stream 30 and the combined feed 33 is passed to second stage IPA formation reactor 34. A mixture of water and IPA exits second stage IPA formation reactor 34 in stream 35 and is routed to azeotrope column 28.

What is claimed:

1. A two-stage process for the production of diisopropyl ether which process comprises the steps of:
  (a) in a first stage, reacting a propylene-containing stream with an isopropyl alcohol recycle stream in the presence of a catalyst in a diisopropyl ether formation reactor under conditions to produce a first stage effluent stream comprising diisopropyl ether and unreacted propylene and isopropyl alcohol;
  (b) passing at least a portion of said first stage effluent stream to a diisopropyl ether/isopropyl alcohol/water separation zone to produce a diisopropyl ether product stream and said isopropyl alcohol recycle stream;

(c) in a second stage, reacting at least a portion of said diisopropyl ether product stream with water in the presence of a catalyst in an isopropyl alcohol formation reactor under conditions sufficient to produce a second stage effluent stream comprising isopropyl alcohol and water;

(d) passing at least a portion of said second stage effluent stream to said diisopropyl ether/isopropyl alcohol/water separation zone; and (e) recycling at least a portion of said isopropyl alcohol recycle stream to said first stage.

2. The process of claim 1 further comprising passing at least a portion of said first stage effluent stream resulting from step (a) to a light ends recovery zone to produce a propylene/propane overhead mixture.

3. The process of claim 2 further comprising passing said propylene/propane overhead mixture to a depropanizer zone to produce a propylene recycle stream.

4. The process of claim 3 further comprising passing said propylene recycle stream to said first stage.

5. The process of claim 1 wherein said propylene-containing stream has a propylene concentration of not more than about 75 wt. %.

6. The process of claim 1 wherein said isopropyl alcohol recycle stream has a water concentration of less than about 3 wt. %.

7. A two-stage process for the production of diisopropyl ether which process comprises the steps of:

(a) in a first stage, reacting a propylene-containing stream having a propylene concentration of not more than about 75 wt. % with an isopropyl alcohol recycle stream in the presence of a catalyst in a diisopropyl ether formation reactor under conditions to produce a first stage effluent stream comprising diisopropyl ether and unreacted propylene and isopropyl alcohol;

(b) passing at least a portion of said first stage effluent stream to a diisopropyl ether/isopropyl alcohol/water separation zone to produce a diisopropyl ether product stream and said isopropyl alcohol recycle stream having a water concentration of less than about 3 wt. %;

(c) in a second stage, reacting at least a portion of said diisopropyl ether product stream with water in the presence of a catalyst in an isopropyl alcohol formation reactor under conditions sufficient to produce a second stage effluent stream comprising isopropyl alcohol and water;

(d) passing at least a portion of said second stage effluent stream to said diisopropyl ether/isopropyl alcohol/water separation zone; and (e) recycling at least a portion of said isopropyl alcohol recycle stream to said first stage.

8. The process of claim 7 further comprising passing at least a portion of said first stage effluent stream resulting from step (a) to a light ends recovery zone to produce a propylene/propane overhead mixture.

9. The process of claim 8 further comprising passing said propylene/propane overhead mixture to a depropanizer zone to produce a propylene recycle stream.

10. The process of claim 9 further comprising passing said propylene recycle stream to said first stage.

11. A two-stage process for the production of diisopropyl ether which process comprises the steps of:

(a) in a first stage, reacting a propylene-containing stream having a propylene concentration of not more than about 75 wt. % with an isopropyl alcohol recycle stream in the presence of a catalyst in a diisopropyl ether formation reactor under conditions to produce a first stage effluent stream comprising diisopropyl ether and unreacted propylene and isopropyl alcohol;

(b) passing at least a portion of said first stage effluent stream to a light ends recovery zone to produce a propylene/propane overhead mixture and a light ends recovery effluent stream;

(c) passing said propylene/propane overhead mixture to a depropanizer zone to produce a propylene recycle stream;

(d) passing said propylene recycle stream to said first stage;

(e) passing at least a portion of said light ends recovery effluent stream to a diisopropyl ether/isopropyl alcohol/water removal zone to produce a diisopropyl ether/isopropyl alcohol/water removal zone effluent stream and said isopropyl alcohol recycle stream having a water concentration of less than about 3 wt. %;

(f) passing at least a portion of said diisopropyl ether/isopropyl alcohol/water removal zone effluent stream to a water wash zone to produce a diisopropyl ether product stream and a water wash stream comprising isopropyl alcohol and water;

(g) passing at least a portion of said water wash effluent stream to an azeotrope column to produce an azeotrope column effluent stream comprising water;

(h) in a second stage, passing said azeotrope effluent stream to an isopropyl alcohol formation reactor and reacting at least a portion of said diisopropyl ether product stream in the presence of a catalyst in said isopropyl alcohol formation reactor under conditions sufficient to produce a second stage effluent stream comprising isopropyl alcohol and water;

(i) passing at least a portion of said second stage effluent stream to said diisopropyl ether/isopropyl alcohol/water separation zone; and (j) recycling at least a portion of said isopropyl alcohol recycle stream to said first stage.

* * * * *